(12) United States Patent  
Luhta et al.

(10) Patent No.: US 9,121,950 B2  
(45) Date of Patent: Sep. 1, 2015

(54) IMAGING DETECTOR

(75) Inventors: Randall Peter Luhta, Chardon, OH (US); Marc Anthony Chappo, Elyria, OH (US); Brian E. Harwood, Kingston Springs, TN (US); Rodney Arnold Mattson, Mentor, OH (US)

(73) Assignee: Koninklijke Philips N.V., Eindhoven (NL)

( * ) Notice: Subject to any disclaimer, the term of this patent is extended or adjusted under 35 U.S.C. 154(b) by 222 days.

(21) Appl. No.: 14/009,678

(22) PCT Filed: Apr. 5, 2012

(86) PCT No.: PCT/IB2012/051685
§ 371 (c)(1),
(2), (4) Date: Oct. 3, 2013

(87) PCT Pub. No.: WO2012/137160
PCT Pub. Date: Oct. 11, 2012

(65) Prior Publication Data
US 2014/0029724 A1    Jan. 30, 2014

Related U.S. Application Data

(60) Provisional application No. 61/472,238, filed on Apr. 6, 2011.

(51) Int. Cl.
*G01T 1/20*    (2006.01)
*G01N 23/04*    (2006.01)

(52) U.S. Cl.
CPC .............. *G01T 1/2018* (2013.01); *G01N 23/04* (2013.01)

(58) Field of Classification Search
CPC ....... G01T 1/24; G01T 1/2928; G01T 1/2018; G01T 1/20; G01T 1/2002; A61B 6/4233; H01L 27/14676
USPC .......... 378/19, 98.8; 250/366, 370.09, 370.11
See application file for complete search history.

(56) References Cited

U.S. PATENT DOCUMENTS

| 5,506,409 | A | 4/1996 | Yoshida et al. |
| 6,608,312 | B1 | 8/2003 | Okada et al. |
| 7,173,998 | B2 | 2/2007 | Hoffman et al. |
| 7,238,945 | B2 | 7/2007 | Hoffman et al. |
| 7,382,854 | B2 | 6/2008 | Hoffman et al. |

(Continued)

FOREIGN PATENT DOCUMENTS

| JP | 09054162 A | 2/1997 |
| JP | 2008224429 A | 9/2008 |
| KR | 20100086098 | 7/2010 |

*Primary Examiner* — Jurie Yun

(57) ABSTRACT

An imaging detector (214) includes a scintillator array (216) including a scintillator element (228) and a material (230) and a photosensor array (218) including a detector element (222) having a light sensitive region (224) and a non-sensitive region (226). The light sensitive region is separated from the scintillator element by a gap, the light sensitive region is in one-to-one mechanical alignment with the scintillator element, and the non-sensitive region is in mechanical alignment with the material. The detector further includes structure (234) that includes one or more material free channels. The structure is located between the non-sensitive region and the material and not between the light sensitive region and the scintillator element. An optical adhesive (232) is located in the gap, filling the entire gap, and mechanically and optically coupling the light sensitive region and the scintillator element.

22 Claims, 7 Drawing Sheets

(56) References Cited

U.S. PATENT DOCUMENTS

| | | | |
|---|---|---|---|
| 7,605,374 B2 * | 10/2009 | Hoggatt et al. | ............... 250/368 |
| 2002/0079459 A1 | 6/2002 | Dorscheid et al. | |
| 2005/0094763 A1 | 5/2005 | Sherman et al. | |
| 2007/0018212 A1 | 1/2007 | Shibayama | |
| 2008/0258067 A1 | 10/2008 | Vogtmeier et al. | |
| 2010/0116995 A1 | 5/2010 | Levene et al. | |

* cited by examiner (A)

(B)

IMAGING DETECTOR

CROSS REFERENCE TO RELATED APPLICATIONS

This application is a national filing of PCT application Serial No. PCT/IB2012/051685, filed Apr. 5, 2012, published as WO 2012/137160 A2 on Oct. 11, 2012, which claims the benefit of U.S. provisional application Ser. No. 61/472,238 filed Apr. 6, 2011, which is incorporated herein by reference.

FIELD OF THE INVENTION

The following generally relates to imaging and more particularly to a scintillator-photodiode based imaging detector of an imaging system, and is described with particular application to computed tomography (CT). However, the following is also amenable to other imaging modalities which employ a scintillator-photodiode based imaging detector.

BACKGROUND OF THE INVENTION

A computed tomography (CT) scanner includes a rotating portion rotatably supported by a stationary portion. The rotating portion supports an x-ray tube, which emits radiation that traverses an examination region, and a detector array that detects radiation traversing the examination region. A conventional integrating detector array includes a scintillator array optically coupled to a photodiode array. The scintillator array absorbs x-ray photons and emits light photons indicative thereof, and the photodiode array receives the light photons and generates electrical signals indicative thereof and hence the absorbed x-ray photons. A reconstructor reconstructs the signals and generates volumetric image data indicative of the examination.

Various approaches have been used to couple the scintillator and detector arrays. One approach is discussed in connection with FIGS. 1A and 1B. FIG. 1A shows a two dimensional photodiode array 102. Generally, such arrays are 16×16 up to 16×64; however, for explanatory purposes, the illustrated array is a 2×2 array with four generally square shaped detector elements 104. Each detector element 104 includes a surface 106 with a light sensitive region 108 surrounded by a non-sensitive region 110. A drop of an optical adhesive 112 is placed at a junction 114 where the four detector pixels 104 meet. A scintillator array 116 is then lowered onto the photodiode array 102. As the scintillator array 116 physically contacts the optical adhesive 112 and applies a force thereon, the optical adhesive 112 radially spreads from the junction 114 over the surface 106, including both the light sensitive regions 108 and the non-sensitive regions 110. FIG. 1B shows the scintillator array 116 lowered onto the photodiode array 102 with the optical adhesive 112 there between.

With this approach, as well as other approaches, optical adhesive voids (or air bubbles) may form and be trapped between the scintillator array 116 and the photodiode array 102. Unfortunately, such voids may decrease light collection efficiency, i.e., inhibit or prevent light transmission from the scintillator array 116 to the light sensitive regions 108 of the photodiode pixels 104. Furthermore, it can be difficult to control the final optical adhesive thickness between the scintillator array 116 and the photodiode array 102, and excess adhesive 118 will squeeze out of the sides, as shown in FIG. 1B, and must be subsequently removed. Moreover, this approach requires fixtures to hold the scintillator array 116 and the photodiode array 102 in place, and the automation machinery generally is expensive.

SUMMARY OF THE INVENTION

Aspects of the present application address the above-referenced matters and others.

According to one aspect, an imaging detector includes a scintillator array including a scintillator element and a material and a photosensor array including a detector element having a light sensitive region and a non-sensitive region. The light sensitive region is separated from the scintillator element by a gap, the light sensitive region is in one-to-one mechanical alignment with the scintillator element, and the non-sensitive region is in mechanical alignment with the material. The detector further includes structure that includes one or more material free channels. The structure is located between the non-sensitive region and the material and not between the light sensitive region and the scintillator element. An optical adhesive is located in the gap, filling the entire gap, and mechanically and optically coupling the light sensitive region and the scintillator element.

According to another aspect, a method includes placing a volume optical adhesive on a light sensitive region of a photosensor array of a detector array; and mechanically coupling, via the optical adhesive, a scintillator array to the photosensor array of the detector array. Mechanically coupling the scintillator array includes applying a force, via the scintillator array, to the optical adhesive as the scintillator array physically contacts the optical adhesive and moves towards the photosensor array, which causes the optical adhesive to spread and entirely fill a gap between the photosensor array and the scintillator array, and at least one of air or excess optical adhesive flows from the gap into one or more material free channels of the detector array located outside of the gap.

According to another aspect, an imaging system includes a source that emits radiation that traverses an examination region and a detector array that detects radiation that traverses the examination region and generates projection data indicative of the detected radiation. The detector array includes a scintillator array having a scintillator element and a photosensor array having a light sensitive element, the scintillator element is in mechanically alignment with and optically coupled to, via an optical coupling, the light sensitive element, the detector array further includes one or more material free channels located about a perimeter of the optical coupling between the scintillator element and the light sensitive element, and the one or more material free channels holds at least one of air or excess optical adhesive.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
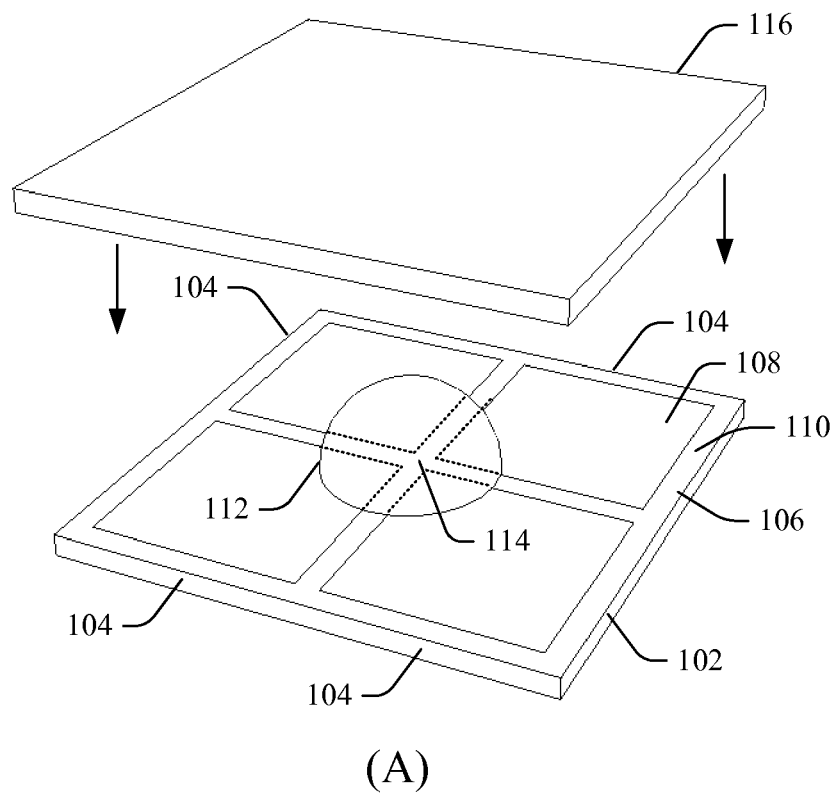
FIGS. 1A and 1B illustrate a prior art approach to coupling a scintillator array and a photodiode array of a detector array.
Figure 1:
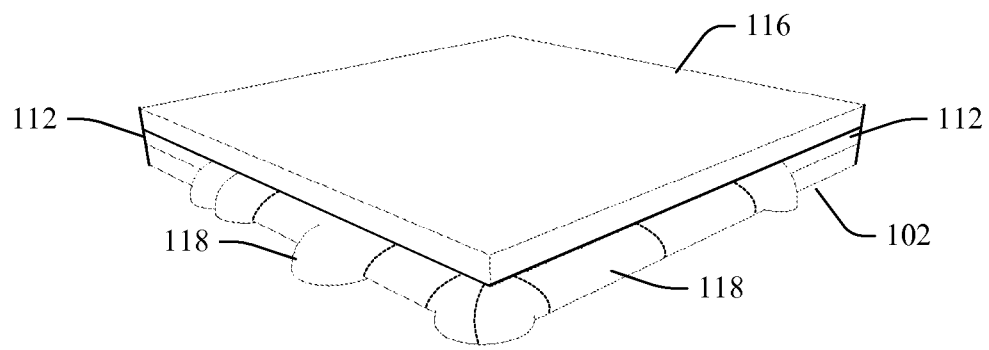
Figure 2:
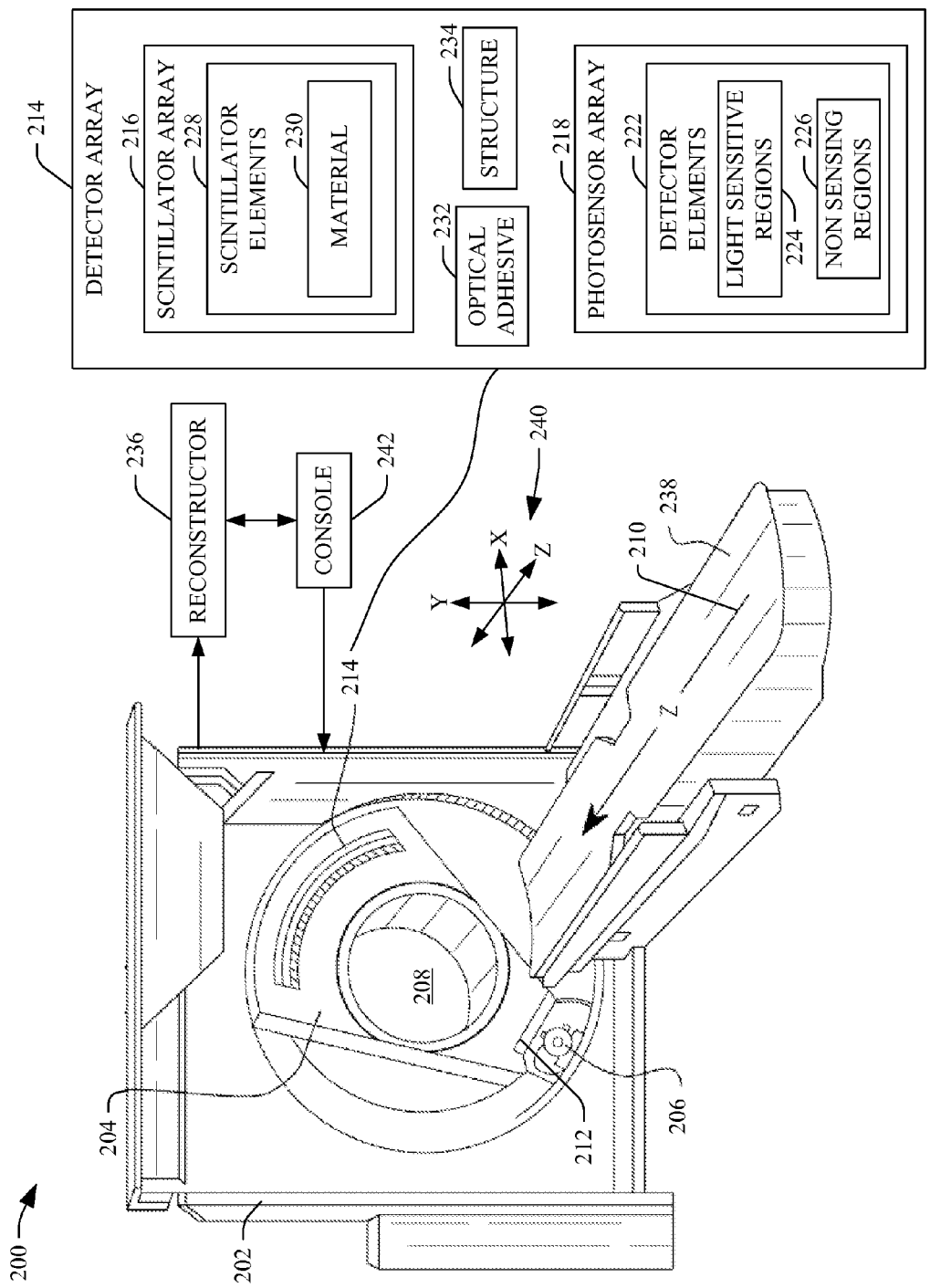
FIG. 2 schematically illustrates an example imaging system in connection with a detector array that includes structure with channels for air and/or excess optical adhesive.

FIG. 2 schematically illustrates an imaging system 200 such as a computed tomography (CT) scanner. The imaging system 200 includes a generally stationary gantry portion 202 and a rotating gantry portion 204. The rotating gantry portion 204 is rotatably supported by the generally stationary gantry portion 202 via a bearing or the like. A radiation source 206, such as an x-ray tube, is supported by the rotating gantry portion 204 and rotates therewith around an examination region 208 about a longitudinal or z-axis 210. A source collimator 212 collimates radiation emitted by the radiation source 206, producing a generally cone, fan, wedge or otherwise-shaped radiation beam that traverse the examination region 208.

A one or two dimensional detector array 214 subtends an angular arc opposite the examination region 208 across from the radiation source 206 and detects radiation that traverses the examination region 208 and generates an electrical signal indicative of the detected radiation. In the illustrated embodiment, the detector array 214 includes a scintillator array 216 optically coupled to a photosensor array 218. The photosensor array 218 includes multiple detector elements 222, each having a light sensitive region 224 (which senses light) at least partially surrounded by a non-sensing region 226 (which does not sense light).

The scintillator array 216 includes complementary scintillator elements 228 that respectively align, in one-to-one manner, with corresponding photodiode array pixels 222 with a gap there between, and material (e.g., such as reflective or other) 230 disposed between the elements 228. The scintillator array 216 absorbs x-ray photons incident thereon and emits light photons indicative of the absorbed x-ray photons, the light sensitive regions 224 receives the light photons, and the photosensor array 218 generates and outputs electrical signals indicative of the light photons and hence the absorbed x-ray photons. The scintillator array 216 is optically coupled to the photosensor array 218 via an optical adhesive 232. The optical coupler can be variously introduced. In one instance, it can be dispensed by a robot via jetting and/or otherwise introduced.

As described in greater detail below, in at least one embodiment, the detector array 214 includes physical structure 234 with one or more material free channels that receive any air and/or excess optical adhesive during assembly. This allows air between the scintillator array 216 and the photosensor array 218 to escape therefrom, mitigating formation of adhesive voids or trapping air between the scintillator array 216 and the photosensor array 218. This may improve light collection efficiency relative to a configuration in which the structure 234 is omitted and air trapped between the scintillator array 216 and the photosensor array 218 inhibits or prevents light emitted by the scintillator array 216 from reaching the photosensor array 218. As further described in greater detail below, the structure 234 is disposed between the scintillator array 216 and the photosensor array 218, part of the scintillator array 216, and/or part of the photosensor array 218. Additionally or alternatively, the structure 234 can be configured to facilitate reducing crosstalk between detector pixels 222, relieving mechanical stress of the detector array 214, preventing radiation damage to detector electronics, improving light collection efficiency, and/or improving an alignment between the scintillator array 216 and the photosensor array 218.

A reconstructor 236 reconstructs the signal generated by the detector array 214 and generates volumetric image data indicative of the examination region 208. The illustrated reconstructor 236 is configured to employ one or more reconstruction algorithms such as a filtered back-projection algorithm, an iterative reconstruction algorithm, and/or other reconstruction algorithm. A subject support 238, such as a couch, supports an object or subject. The subject support 238 is configured to position, in connection with respect to an x, y, and/or z frame of reference 240, the object or subject with respect to the examination region 208, before, during and/or after scanning the object or subject. A general purpose computing system serves as an operator console 242, and includes an output device such as a display, an input device such as a keyboard, mouse, and/or the like, one or more processor and computer readable storage medium (e.g., physical memory). The console 242 allows the operator to control operation of the system 200, for example, allowing the operator to initiate scanning, etc.

Figure 3:
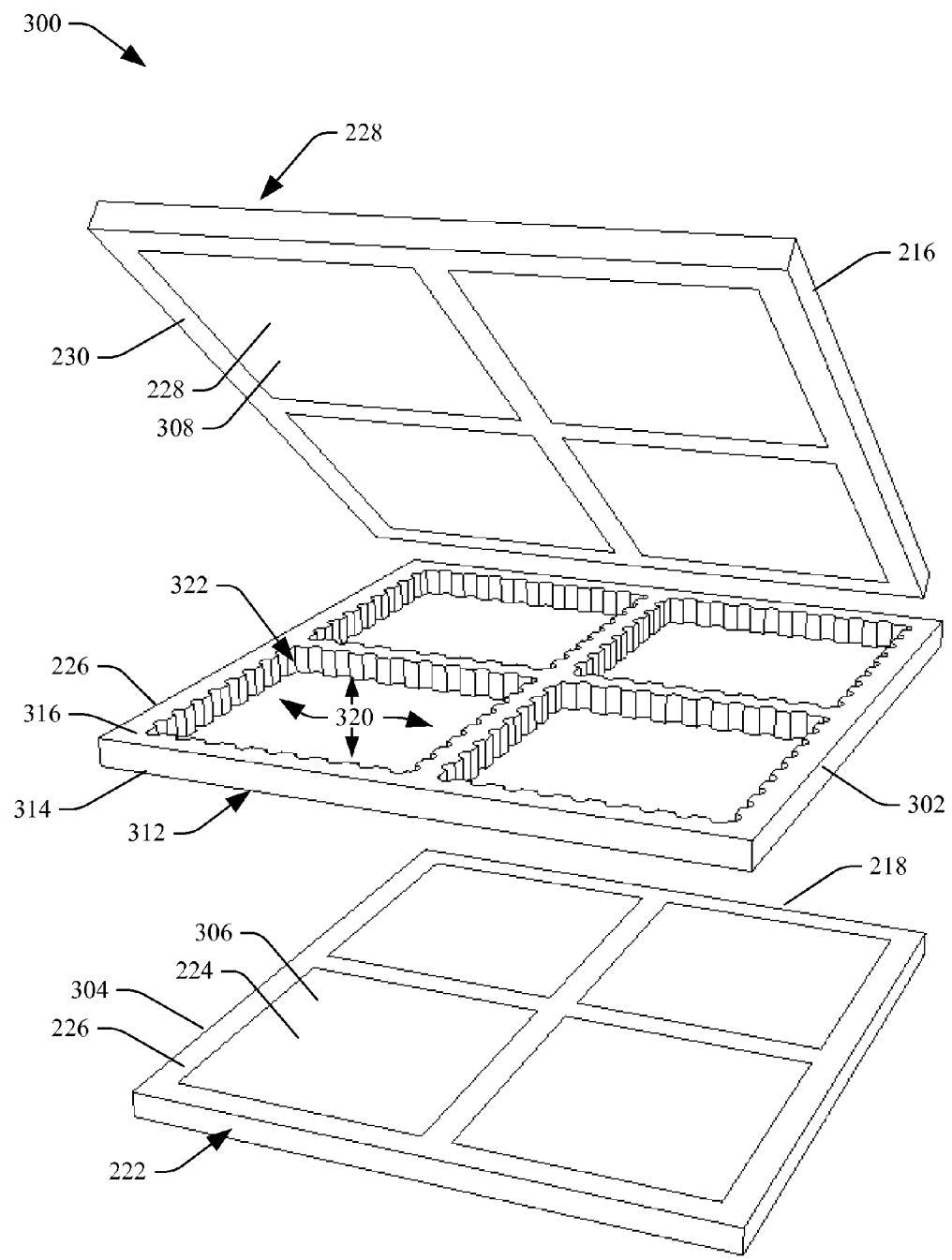
FIG. 3 schematically illustrates an example of the detector array without the optical adhesive.
Figure 4:
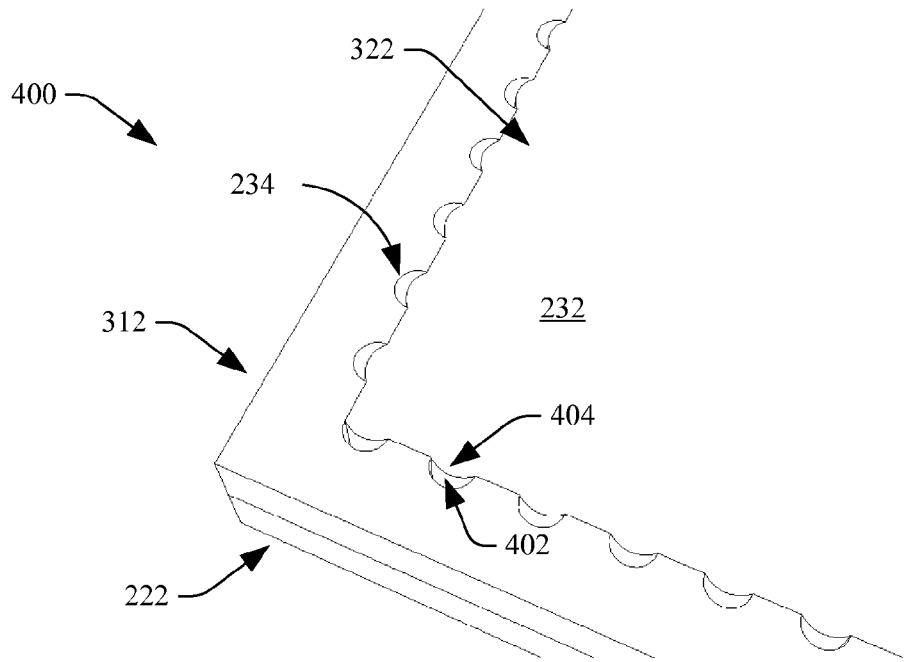
FIG. 4 schematically illustrates a portion of the example of the detector array with the optical adhesive.
Figure 5:
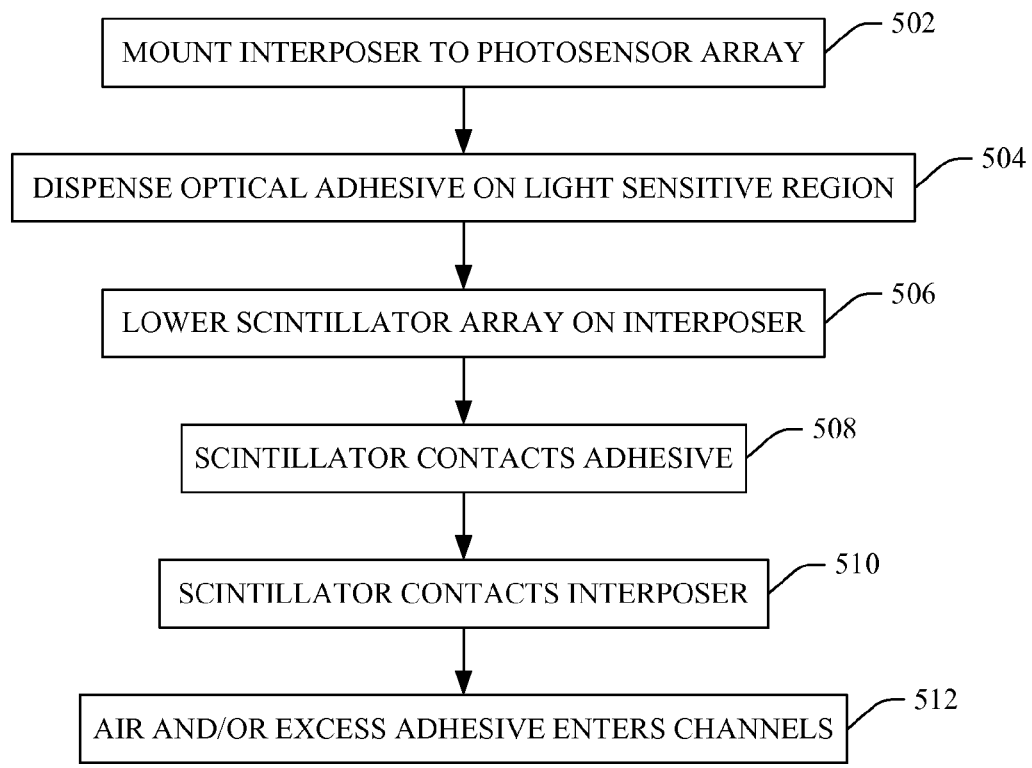
FIGS. 5, 6, 7 and 8 illustrate an example method for assembling the detector array.

FIGS. 3 and 4 respectively illustrate example portions 300 and 400 of the detector array 214 in which the structure 234 is part of an interposer 302 that is disposed between the scintillator array 216 and the photosensor array 218. The following describes the interposer 302 in connection with a single detector element 222 of the sub-portions 300 and 400.

Initially referring to FIG. 3, the scintillator array 216, the interposer 302 and the photosensor array 218 are shown separated and the optical adhesive 232 is omitted for explanatory purposes. The illustrated portion of the scintillator array 216, interposer 302 and photosensor array 218 includes 2×2 arrays. Likewise, FIGS. 6, 7, 9, and 10 (described below) show 2×2 arrays. However, the arrays 216, 214 and 218 can be on the order of 16×16, 16×64, and/or other dimension arrays are contemplated herein.

The photosensor array 218 includes a detector element 222 having a surface 304 with a light sensitive region 224 and a surface 306 and a non-sensitive region 226 around the surface 306 of the light sensitive region 224. The scintillator array 216 includes a corresponding scintillator element 228 having a surface 308 surrounded by a material 230. A geometry of the surface 308 of the scintillator element 228 substantially matches (is the same as or close to the same as) a geometry of the surface 306 of the light sensitive region 224.

The interposer 302 includes an interposer element 312, having a first surface 314 with a width that is less than a width of the non-sensitive region 226 and a second surface 316 with a width that is less than a width of the material 230. The widths of the surfaces 314 and 316 are less than the widths of the non-sensitive region 226 and the material 230 in that when the interposer element 312 is disposed between the detector element 222 and the scintillator element 228, the interposer element 312 lies only within the region between the non-sensitive region 226 and the material 230 and not over the light sensitive region 224 or the scintillator element 228.

The illustrated interposer element 312 includes inner walls 320 facing each other and defining an aperture 322 there between and a gap between the scintillator array 216 and the photosensor array 218. In the illustrated embodiment, the inner walls 320 provide a continuous surface and the channels are formed in the inner walls 320 and also reside only between the detector element 222 and the scintillator element 228. The channels are adjacent to and accessible from the aperture 322, which is the region between the light sensitive region 224 and the scintillator element 228. In this example, the channels have a meandering contour or pattern, forming a series of contiguous semi-circles. Other contours or pattern are also contemplated herein.

The interposer element 312 has a predetermined non-zero depth, which is substantially the same for any particular detector array 214, but may be different for different detector arrays 214. Increasing the depth facilitates decreasing mechanical stress. The interposer 302 can include metal, plastic, a reflective or absorptive powder in an epoxy binder (e.g., barium sulfide), and/or other materials.

FIG. 4 shows a portion of the detector element 222 with the interposer element 312 affixed thereto and with the optical adhesive 232 in the aperture 322.

The scintillator element 228 is not shown in the example in order to discuss the optical adhesive 232. In this example, the optical adhesive 232 fills the entire space between the light sensitive region 224 and the scintillator element 228, and conforms to the contours of the surfaces 308 and 306 such that no or substantially no air exists between the surfaces 308 and 306. In the illustrated embodiment, air 402 and excess adhesive 404 are in the channels and only between the non-sensitive region 226 and the material 230, and not between the light sensitive region 224 and the scintillator element 228.

Generally, a surface tension of the optical adhesive 232 causes the optical adhesive to uniformly fill the entire region between light sensitive region 224 (not visible) and the scintillator element 228 (not visible) and inhibits optical adhesive, which would otherwise be between the light sensitive region 224 and the scintillator element 228, from leaving the space between the light sensitive region 224 and the scintillator element 228 due to an external force and filling the channels, allowing air back into the space between the light sensitive region 224 and the scintillator element 228. Only the air 402 and/or the adhesive in excess of the amount that can fit between the light sensitive region 224 and the scintillator element 228 flows into the channels.

FIGS. 5, 6, 7 and 8 describe an approach for assembling the detector array 214.

Figure 6:
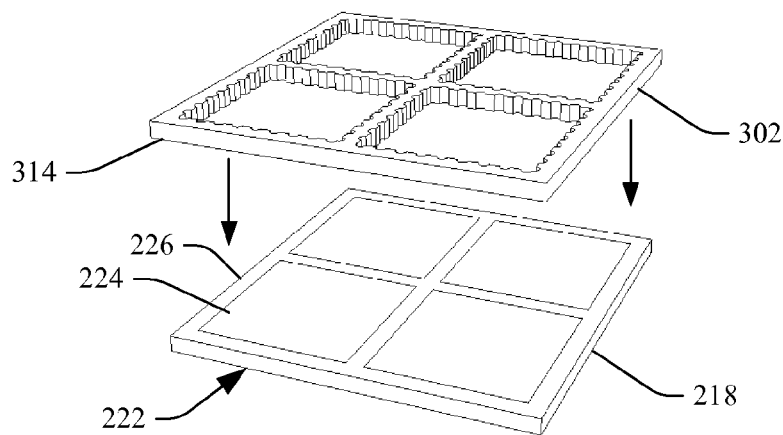

At 502, the interposer 302 is mounted to the photosensor array 218. As described herein, the surface 314 of the interposer 302 affixes only to the non-sensitive regions 226 and not to the light sensitive regions 224 of the photosensor array 218. This is shown in FIG. 6.

Figure 7:
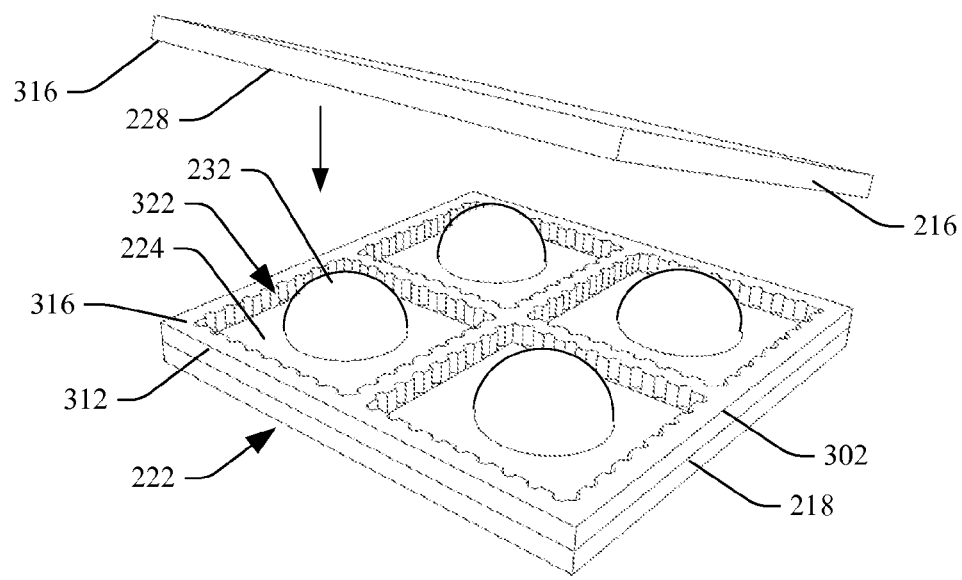

At 504, the optical adhesive 232 is dispensed on the surfaces 306 of each of the detector elements 222 within the apertures 322 of the corresponding interposer elements 312. This is shown in FIG. 7.

At 506, the scintillator array 216 is lowered onto the interposer 302. As described herein, the surface 316 of the interposer 302 affixes only to the material 230 of the scintillator array 216. This is also shown in FIG. 7.

At 508, the scintillator array 216, when being lowered, physically contacts the optical adhesive 232, causing the optical adhesive 232 to spread out and fill the entire space between the light sensitive region 224 and the scintillator element 228.

Figure 8:
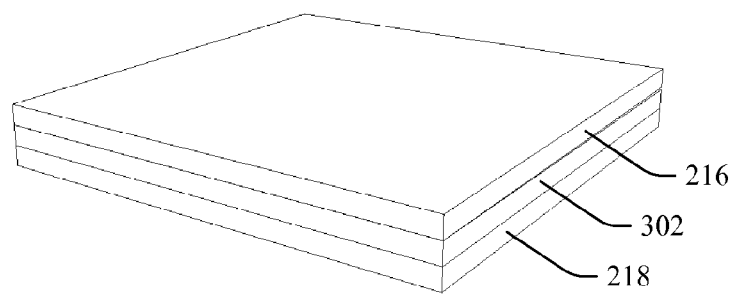

At 510, the scintillator array 216 comes into contact with the interposer 302/photosensor array 218 assembly. This is shown in FIG. 8.

At 512, any air 402 and/or excess adhesive 404 between the scintillator array 216 and the photosensor array 218 enters the channels of the structure 234.

It is to be appreciated that the ordering of the above acts is not limiting. As such, other orderings are contemplated herein. In addition, one or more acts may be omitted and/or one or more additional acts may be included, and/or one or more acts may occur concurrently.

The above acts can be done manually and automated via suitable machinery.

Optionally, the photosensor array 218, the interposer 302 and/or the scintillator array 216 may include one or more features that facilitate aligning the photosensor array 218, the interposer 302 and/or the scintillator array 216 with each other. An example of such features is shown in connection with FIG. 9.

Figure 9:
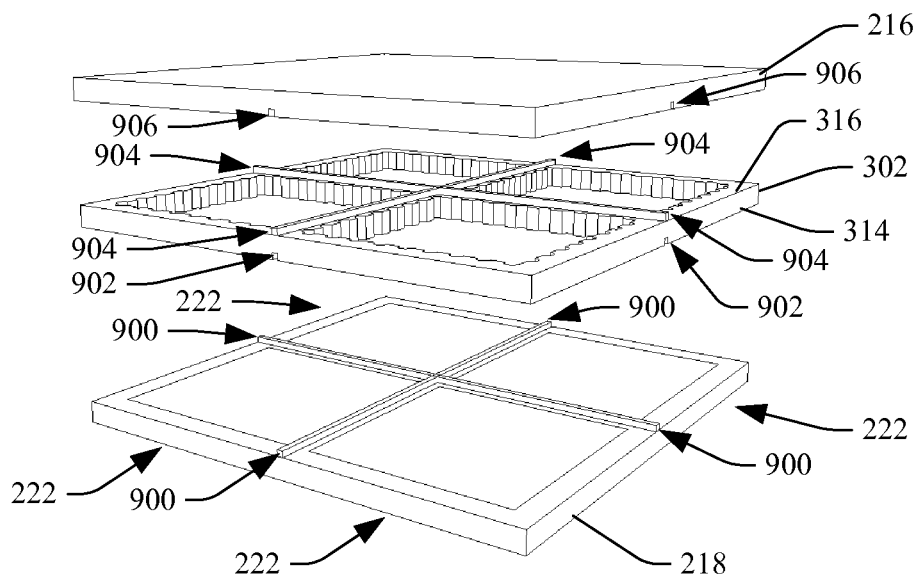
FIG. 9 schematically illustrates an example of the detector array with alignment features.

In FIG. 9, the photosensor array 218 includes raised alignment features 900 on the non-sensitive regions 226, between the detector elements 222. The raised alignment features 900 may be part of the photosensor array 218 or affixed thereto. The interposer 302 includes complementary alignment slots 902 on the surface 314. When coupling the interposer 302 and the photosensor array 218, the alignment features 900 align with the slots 902, thereby aligning the interposer 302 and the photosensor array 218.

The interposer 302 further includes raised alignment features 904 on the surface 316. The raised alignment features 904 may be part of the interposer 302 or affixed thereto. The scintillator 216 includes complementary alignment slots 906. When coupling the scintillator 216 and the interposer 302, the alignment features 904 align with the slots 906, thereby aligning the scintillator 216 with the interposer 302 and hence the photosensor array 218.

In another embodiment, at least one of the raised alignment features 900 and 904 and/or corresponding alignment slots 902 and 906 are not included. In yet another embodiment, the raised alignment features 900 and 904 and/or corresponding alignment slots 902 and 906 may be differently shaped. For example, rather than elongate structures shown in FIG. 9, the raised alignment features can be pins, and the alignment slots can be complementary recesses.

The raised features 900 and 904 can be formed during photosensor array 218 and/or interposer 302 fabrication using a metallic or non-metallic film deposition. A suitable fabrication may utilize photolithographic techniques. Alternatively, the raised features 900 and 904 can be affixed to the photosensor array 218 and/or interposer 302 after fabrication of the photosensor array 218. The complementary alignment slots 902 and 906 in the scintillator array 216 and/or interposer 302 can be formed via mechanical saw, laser, and/or other technique.

Variations are contemplated.

In a variation, the interposer 302 is formed as part of the photosensor array 218 in the non-sensitive area 110.

The interposer 302 may also facilitate mitigating radiation damage. For instance, the interposer 302 may additionally or alternatively include an x-ray absorbing material that can prevent radiation from reaching the photodiode and/or electronics.

Additionally or alternatively, the interposer 302 facilitate reducing crosstalk. For instance, the interposer 302 may include an opaque material.

Additionally or alternatively, the interposer 302 facilitate increasing light collection efficiency. For instance, the interposer 302 may include a whiter reflective material.

Additionally or alternatively, the interposer 302 facilitate decreasing mechanical stress of the detector array 214. For instance, when configured to reduce crosstalk, a thicker interposer 302 can also be used, which can facilitate decreasing mechanical stress of the detector array 214.

In the illustrated embodiments, the interposer element 312 is for a single detector element 222. In another embodiment, a single interposer element 312 may cover more that just a single detector element 222. In this instance, the aperture 322 will cover more then just one light sensitive region 224.

In the illustrated embodiments, the photosensor array 218 includes the raised alignment features 900 and the scintillator array 216 includes slots 906. In another embodiment, the photosensor array 218 includes the slots and the scintillator array 216 includes raised features. The interpose 302 is accordingly adjusted. In yet another embodiment, at least one of the photosensor array 218 or the scintillator array 216 includes both raised features and slots.

Figure 10:
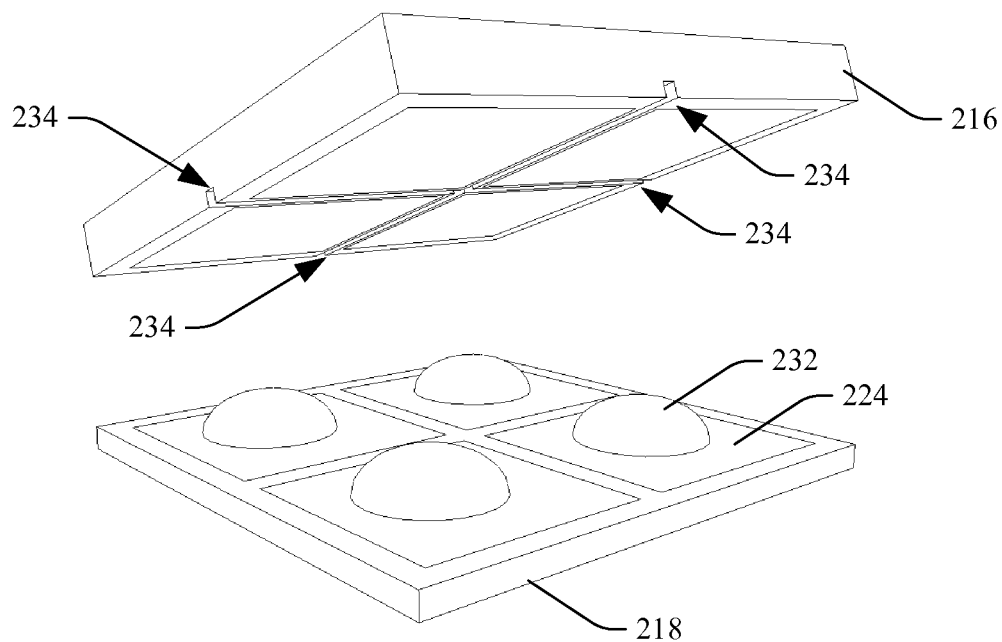
FIGS. 10 and 11 schematically illustrate an example of the detector array in which the channels are part of a scintillator array of the detector array.
Figure 11:
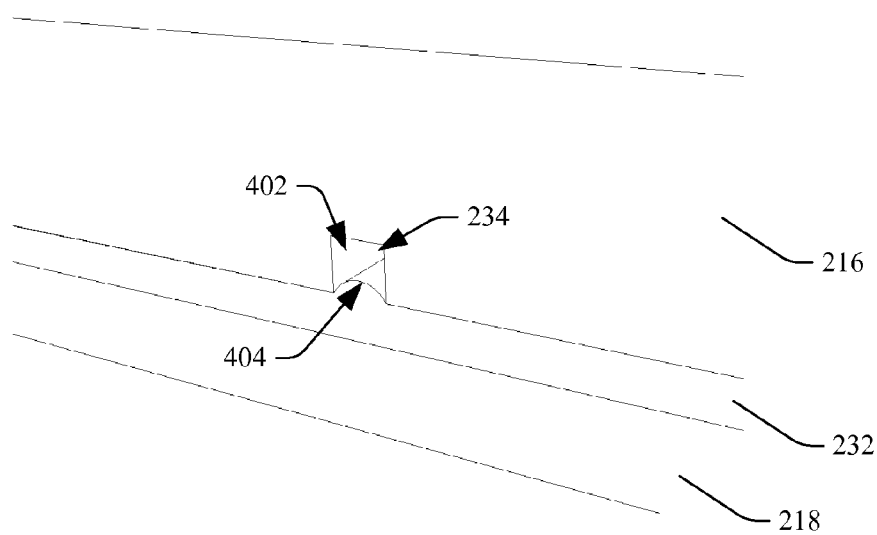

In FIGS. 5-8, the interposer 302 is first affixed to the photosensor array 218 and then the scintillator array 216 is affixed to the interposer 302/photosensor array 218 assembly. In another embodiment, the interposer 302 is first affixed to the scintillator array 216 and then the photosensor array 218 is affixed to the interposer 302/scintillator array 216 assembly FIGS. 10 and 11 illustrate an embodiment in which the scintillator array 216 includes the structure 234 with the channels and the interposer 302 is omitted. In this embodiment, the structure 234 and hence the channels extend along the material 230. The channels can be form via mechanical saw, laser, and/or other technique. Similar to the embodiment described in connection with FIGS. 5-8, optical adhesive 232 is applied to the light sensitive regions 224 (as shown in FIG. 10), the scintillator array 216 is lowered onto the photosensor array 218, and any air 402 and/or excess adhesive 404 between the scintillator array 216 and the photosensor array 218 flows into the channels 234 (as shown in FIG. 11).

Figure 12:
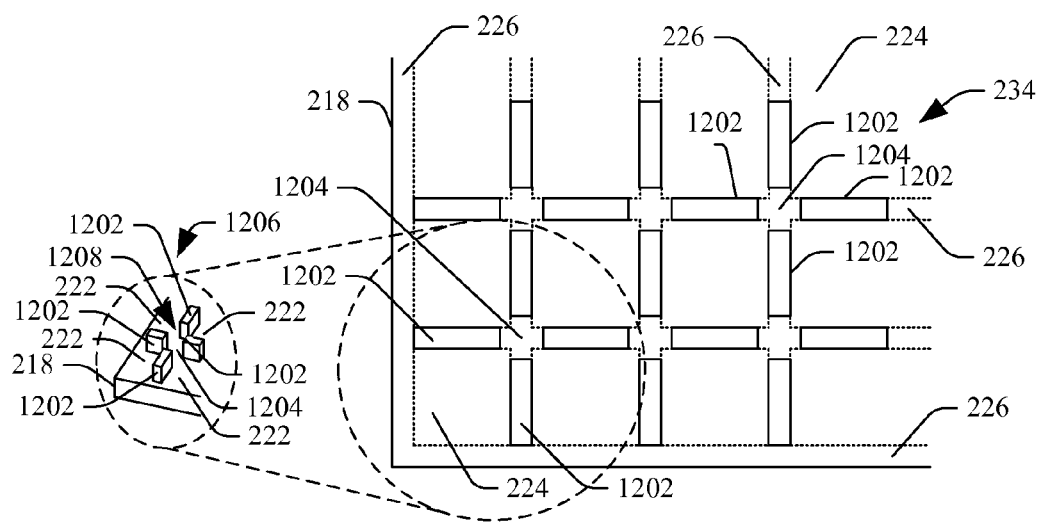
FIG. 12 schematically illustrates an example of the structure with the channels formed on a photosensor array 218 of the detector array.

FIG. 12 schematically illustrates a top down view (looking into the photosensor array 218) of an embodiment in which the structure 234 is part of the photosensor array 218. By way of non-limiting example, the photosensor array 218 may include a metallic, plastic, etc. layer such as a thin film over the light sensitive 224 and non-sensitive regions 226, and photolithography or other known micro-fabrication process may be used to selectively remove parts of the layer where parts that are not removed form the structure 234. Alternatively, the structure 234 may be deposited on the scintillator array 116.

In FIG. 12, the interposer 302 includes a plurality of sub-structures 1202, which are located over and only within portions of the non-sensitive regions 226 that are between light sensitive regions 224, and not over the outer peripheral non-sensitive regions 226 or the non-sensitive regions 226 between sub-structures 1202 at a junction 1204 adjacent of detector elements 222. A perspective view of four detector elements 222 and the corresponding sub-structures 1202 at the junction 1204 for a corner region of the detector array 214 is shown at 1206. A material free region, 1208 located at the junction 1204 and between the sub-structures 1202, forms the channel in which air and/or excess adhesive can flow into. Other patterns are also contemplated herein.

Optionally, a tape (not shown) or the like can be applied over from the scintillator array 216 to the photosensor array 218, over the optical adhesive 232 in the gap therebetween. Such tape may prevent excess adhesive from flowing out of the sides of detector elements 222 where there is no neighboring detector element 222. This includes corner detector elements 222 and detector elements 222 along the edges of the detector array 214.

In another embodiment, at least one of a scintillator element 228 or a detector element 222 includes a hole that extends from the gap between the scintillator element 228 and the detector element 222 to outside of the detector array 214. This hole behaves similar to the structure 234 with the channels described herein, providing a path for air and/or excess adhesive between the scintillator element 228 and the detector element 222 to leave the region between the scintillator element 228 and the detector element 222.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. An imaging detector, comprising:
   a scintillator array including a scintillator element and a material;
   a photosensor array including a detector element having a light sensitive region and a non-sensitive region, wherein the light sensitive region is separated from the scintillator element by a gap, the light sensitive region is in one-to-one mechanical alignment with the scintillator element, and the non-sensitive region is in mechanical alignment with the material;
   structure that includes one or more material free channels, wherein the structure is located between the non-sensitive region and the material and not between the light sensitive region and the scintillator element; and
   an optical adhesive located in the gap, filling the entire gap, and mechanically and optically coupling the light sensitive region and the scintillator element.

2. The imaging detector of claim 1, wherein the one or more material free channels are adjacent to the gap.

3. The imaging detector of claim 1, wherein the one or more material free channels are accessible to a substance in the gap.

4. The imaging detector of claim 1, wherein at least one of the one or more material free channels provides a reservoir that holds air that would otherwise be trapped in the gap between the light sensitive region and the scintillator element.

5. The imaging detector of claim 1, wherein the one or more material free channels provides a reservoir that holds any excess optical adhesive that does not fit in the gap between the light sensitive region and the scintillator element.

6. The imaging detector of claim 1, wherein the structure is part of an interposer (302) disposed between the photosensor array and the scintillator array.

7. The imaging detector of claim 6, wherein a depth of the interposer defines a depth of the gap.

8. The imaging detector of claim 6, wherein the interposer includes an x-ray absorbing material that blocks x-rays impinging on the interposer.

9. The imaging detector of claim 6, wherein the interposer includes a material that reflects light impinging on the interposer towards the light sensitive region.

10. The imaging detector of claim 6, wherein the interposer (302) decreases a mechanical stress of the imaging detector.

11. The imaging detector of claim 6, further including at least first and second complementary alignment features and third and fourth complementary alignment features, wherein one of the first or second complementary alignment features is located on the photosensor array and the other of the first or second complementary alignment features is located on the interposer, one of the third or fourth complementary alignment features is located on the scintillator array and the other of the third or fourth complementary alignment features is located on the interposer, and the alignment features align the photosensor array and the interposer and the scintillator array and the interposer, thereby aligning the photosensor array and the scintillator array.

12. The imaging detector of claim 11, wherein at least one of the complementary features is a protrusion and the other of the complementary features is a complementary recess.

13. The imaging detector of claim 1, wherein the structure is part of the photosensor array.

14. The imaging detector of claim 1, wherein the structure is part of the scintillator array.

15. A method, comprising:
placing a volume optical adhesive on a light sensitive region of a photosensor array of a detector array; and
mechanically coupling, via the optical adhesive, a scintillator array to the photosensor array of the detector array, wherein mechanically coupling the scintillator array includes applying a force, via the scintillator array, to the optical adhesive as the scintillator array physically contacts the optical adhesive and moves towards the photosensor array, which causes the optical adhesive to spread and entirely fill a gap between the photosensor array and the scintillator array, and at least one of air or excess optical adhesive flows from the gap into one or more material free channels of the detector array located outside of the gap.

16. The method of claim 15, wherein the material free channels are part of an interposer, and further comprising: disposing the interposer between the photosensor array and the scintillator array.

17. The method of claim 16, wherein the interposer includes at least one alignment feature, and further comprising: aligning the photosensor array and the scintillator array via the at least one alignment feature.

18. The method of claim 15, wherein the material free channels are part of structure of the photosensor array.

19. The method of claim 18, wherein the structure is formed on the photosensor array via micro-fabrication.

20. The method of claim 15, wherein the material free channels are part of the scintillator array.

21. The method of claim 20, wherein the material free channels include recesses in the scintillator array.

22. An imaging system, comprising:
a source that emits radiation that traverses an examination region,
a detector array that detects radiation that traverses the examination region and generates projection data indicative of the detected radiation;
wherein the detector array includes a scintillator array having a scintillator element and a photosensor array having a light sensitive element, the scintillator element is in mechanically alignment with and optically coupled to, via an optical coupling, the light sensitive element, the detector array further includes one or more material free channels located about a perimeter of the optical coupling between the scintillator element and the light sensitive element, and the one or more material free channels holds at least one of air or excess optical adhesive.

* * * * *